United States Patent [19]
Hendriks et al.

[11] Patent Number: 6,117,979
[45] Date of Patent: Sep. 12, 2000

[54] PROCESS FOR MAKING A BIOPROSTHETIC DEVICE AND IMPLANTS PRODUCED THEREFROM

[75] Inventors: Marc Hendriks, Brunssum; Michel Verhoeven, Maastricht; Patrick Cahalan, Geleen; Raymond Zeeman, Twente; Piet Dijkstra, Twente; Jan Feijen, Twente, all of Netherlands

[73] Assignee: Medtronic, Inc., Minneapolis, Minn.

[21] Appl. No.: 08/912,392

[22] Filed: Aug. 18, 1997

[51] Int. Cl.⁷ .............................. A61K 38/17; A61F 2/02
[52] U.S. Cl. .................... 530/356; 530/840; 525/54.1; 623/11; 623/12; 623/900; 623/901
[58] Field of Search .................... 530/356, 840; 525/54.1; 623/11, 12, 900, 901

[56] References Cited

U.S. PATENT DOCUMENTS

| | | | |
|---|---|---|---|
| 4,806,595 | 2/1989 | Noishiki et al. | 525/54.2 |
| 5,080,670 | 1/1992 | Imamura et al. | 623/2 |
| 5,162,430 | 11/1992 | Rhee et al. | 525/54.1 |
| 5,264,214 | 11/1993 | Rhee et al. | 424/422 |
| 5,279,612 | 1/1994 | Eberhardt | 8/94.11 |
| 5,292,802 | 3/1994 | Rhee et al. | 525/54.1 |
| 5,304,595 | 4/1994 | Rhee et al. | 525/54.1 |
| 5,306,500 | 4/1994 | Rhee et al. | 424/422 |
| 5,308,889 | 5/1994 | Rhee et al. | 523/113 |
| 5,324,775 | 6/1994 | Rhee et al. | 525/54.2 |
| 5,328,955 | 7/1994 | Rhee et al. | 525/54.1 |
| 5,352,240 | 10/1994 | Ross | 623/2 |
| 5,376,375 | 12/1994 | Rhee et al. | 424/423 |
| 5,413,791 | 5/1995 | Rhee et al. | 424/422 |
| 5,428,022 | 6/1995 | Palefsky et al. | |
| 5,446,091 | 8/1995 | Rhee et al. | 525/54.1 |
| 5,447,536 | 9/1995 | Girardot et al. | 8/94.11 |
| 5,470,911 | 11/1995 | Rhee et al. | 525/54.1 |
| 5,475,052 | 12/1995 | Rhee et al. | 525/54.1 |

*Primary Examiner*—Nathan M. Nutter
*Attorney, Agent, or Firm*—Thomas F. Woods; Michael J. Jaro; Harold Patton

[57] ABSTRACT

Bioprosthetic devices made of collagen-based material having collagen amine groups and collagen carboxyl groups are provided as well as methods for their formation. The methods comprise combining an epoxy functionalized crosslinking agent with the collagen-based material in an aqueous medium at an acidic pH to react a portion of the collagen carboxyl groups with the epoxy functionalized crosslinking agent to form crosslinked collagen-based material comprising residual collagen carboxyl groups.

28 Claims, 5 Drawing Sheets

PROCESS FOR MAKING A BIOPROSTHETIC DEVICE AND IMPLANTS PRODUCED THEREFROM

BACKGROUND OF THE INVENTION

Prosthetic implants, which can be made from natural or synthetic materials, include, for example, heart valves, vascular grafts, urinary bladder prostheses, and tendon prostheses. Bioprostheses (i.e., prostheses derived from natural tissue) are typically preferred over synthetic or mechanical prostheses. For example, natural tissue valves are preferred over mechanical valves because tissue valves stimulate the natural flow of the blood better than mechanical valves. Also, no blood anticoagulants are needed when natural tissue valves are used.

Tissue heart valve prostheses are typically made from either porcine aortic valves or bovine pericardium. Such valves are typically made by pretreating the tissue with glutaraldehyde or other crosslinking agent, as discussed below, and sewing the tissue into a flexible metallic alloy or polymeric stent. Such animal tissues mainly consist of collagen and elastin. These components provide the tissues, particularly heart valves, with their needed mechanical strength and flexibility.

Collagen-based materials, including whole tissue, are finding increased use in the manufacture of biomedical devices, such as prosthetic implants. This is particularly true for heart valves. Collagen is a naturally occurring protein featuring good biocompatibility. It is the major structural component of vertebrates, forming extracellular fibers or networks in practically every tissue of the body, including skin, bone, cartilage, and blood vessels. In medical devices, collagen provides a more physiological, isotropic environment that has been shown to promote the growth and function of different cell types, facilitating the rapid overgrowth of host tissue after implantation.

Basically, three types of collagen-based materials can be identified, based on the differences in the purity and integrity of the collagen fiber bundle network initially present in the material. The first type includes whole tissue including noncollagenous substances or cells. As a result of using whole tissue, the naturally occurring composition and the native strength and structure of the collagen fiber bundle network are preserved. Whole tissue xenografts have been used in construction of heart valve prostheses, and also in vascular prostheses. However, the presence of soluble proteins, glycoproteins, glycosaminoglycans, and cellular components in such whole tissue xenografts may induce an immunological response of the host organism to the implant.

The second type of collagen-based material includes only the collagen matrix without the noncollagenous substances. The naturally occurring structure of the collagen fiber bundle network is thus preserved, but the antigenicity of the material is reduced. The fibrous collagen materials obtained by removing the antigenic noncollagenous substances will generally have suitable mechanical properties.

The third type of collagen-based material is purified fibrous collagen. Purified collagen is obtained from whole tissue by first dispersing or solubilizing the whole tissue by either mechanical or enzymatic action. The collagen dispersion or solution is then reconstituted by either air drying, lyophilizing, or precipitating out the collagen. A variety of geometrical shapes like sheets, tubes, sponges or fibers can be obtained from the collagen in this way. The resulting materials, however, do not have the mechanical strength of the naturally occurring fibrous collagen structure.

A major problem in the use of collagen-based materials, and especially whole tissue xenografts, in which the donor and recipient are phylogenetically distant, for implantation is that these materials are prone to hyperacute rejection. This is a rapid and violent rejection reaction that leads to the destruction of the xenograft. Hyperacute rejection appears to be triggered by components of natural immunity, most notably natural antibodies and complement.

In order to use collagen-based materials in manufacturing medical devices, particularly bioprosthetic implants, their durability and in vivo performance typically need to be improved. This can be done by crosslinking the material. Crosslinking of collagen-based materials is used to suppress the antigenicity of the material in order to prevent the hyperacute rejection reaction. In addition, crosslinking is used to improve mechanical properties and enhance resistance to degradation.

Crosslinking can be performed by means of physical methods, including, for example, UV irradiation and dehydrothermal crosslinking. These methods result in a direct, but generally low density crosslinking. Several chemical crosslinking methods for collagen-based materials are known. These methods involve the reaction of a bifunctional reagent with the amine groups of lysine or hydroxylysine residues on different polypeptide chains or the activation of carboxyl groups of glutamic and aspartic acid residues followed by the reaction with an amine group of another polypeptide chain to give an amide bond.

Compared with other known methods, glutaraldehyde (GA) crosslinking of collagen provides materials with the highest degree of crosslinking. It is currently the most frequently used chemical crosslinking reagent for collagen-based materials. Glutaraldehyde is a five carbon aliphatic molecule with an aldehyde at each end of the chain rendering it bifunctional. The aldehyde is able to chemically interact with amino groups on collagen to form chemical bonds. This crosslinking agent is readily available, inexpensive, and forms aqueous solutions that can effectively crosslink tissue in a relatively short period. Using GA crosslinking, increased resistance to biodegradation, reduced antigenicity, and improved mechanical properties of collagen-based materials can be achieved. Despite improved host acceptance, crosslinking of collagen-based materials using GA has shown to have cytotoxic characteristics, both in vitro and in vivo. Also, crosslinking of collagen-based materials using GA tends to result in stiffening of the material and calcification.

Crosslinking can also be accomplished with diisocyanates by bridging of amine groups on two adjacent polypeptide chains. In the first step, reaction of the isocyanate group with a (hydroxy)lysine amine group occurs, resulting in the formation of a urea bond. Thereafter a crosslink is formed by reaction of the second isocyanate group with another amine group. Diisocyanates do not show condensation reactions as observed in GA crosslinking. Also, no residual reagents are left in the material. A disadvantage, however, is the toxicity of diisocyanates and limited water solubility of most diisocyanates.

Another method of crosslinking involves the formation of an acyl azide. The acyl azide method involves the activation of carboxyl groups in the polypeptide chain. The activated groups form crosslinks by reaction with collagen amine groups of another chain. First, the carboxyl groups are esterified by reaction with an alcohol. This ester is then converted to a hydrazide by reaction with hydrazine ($H_2N$—$NH_2$). Acyl azide groups are formed by reaction with an acidic solution of sodium nitrite. At low temperatures and basic pH values, the acyl azide group reacts with a primary amine group to give amide bonds. This multi-step reaction results in good material properties; however, long reaction times (e.g., 7 days) are necessary. Alternatively, a method has recently been developed that does not need an esterification step or the use of hydrazine. In this method, a carboxyl group is converted to an acyl azide group in one single step by reaction with diphenylphosphorylazide (DPPA). This increases the reaction rate significantly; however, the reaction is carried out in an organic solvent (e.g., DMF), which is undesirable.

Also, water-soluble carbodiimides can be used to activate the free carboxyl groups of glutamic and aspartic acid moieties in collagen. Activation of the carboxyl groups with carbodiimides, such as 1-ethyl-3-(3-dimethyl aminopropyl) carbodiimide.HCl (EDC), gives O-acylisourea groups. A condensation reaction by nucleophilic attack of a free amine group of a (hydroxy)lysine residue with urea as a leaving group results in formation of an amide crosslink. The O-acylisourea can also be hydrolyzed or rearranged to an N-acylurea, which is much more stable and will not react to form a crosslink. Addition of N-hydroxysuccinimide (NHS) prevents this rearrangement, however. In the presence of NHS, the O-acylisourea can be converted to an NHS activated carboxyl group, which also can react with a free amine group to form a crosslink. Addition of NHS increases the reaction rate. Also, crosslinking with EDC and NHS provides collagen material with a high degree of crosslinking; however, it also results in a material with a low tensile strength.

Yet another crosslinking method uses epoxy compounds to crosslink collagen. See, for example, U.S. Pat. Nos. 4,806,595 (Noishiki et al.) and 5,080,670 (Imamura et al.). Epoxy compounds (i.e., epoxides) can undergo both acid-catalyzed and base-catalyzed reactions with a number of functional groups, including amine groups and carboxyl groups, under the appropriate conditions. Typically, however, crosslinking of collagen is carried out at basic pH (e.g., pH 8–10) with the result that crosslinking occurs through the free amine groups of the collagen. Although such material is generally stable to hydrolysis and enzymatic degradation, it has generally poor mechanical properties (e.g., low tensile strength).

Thus, there still exists a need for methods of crosslinking collagen-based materials that have both good mechanical properties and stability toward hydrolysis and enzymatic degradation.

SUMMARY OF THE INVENTION

The present invention provides methods of making a bioprosthetic device (typically, an implant or implantable device) comprising collagen-based material. The methods involve crosslinking the collagen-based material. Significantly, the methods of the present invention yield a material with a generally high degree of crosslinking and a generally high resistance towards enzymatic digestion, while the material maintains a relatively high degree of flexibility without substantial stiffening over time. This material is also preferably highly hydrophilic, which is believed to increase the biocompatibility of the material. The methods of the present invention are particularly suitable for crosslinking cardiovascular bioprostheses, such as heart valves and vascular grafts.

Accordingly, a method for making a bioprosthetic device made of collagen-based material having collagen amine groups and collagen carboxyl groups is provided. The method comprises combining an epoxy functionalized crosslinking agent with the collagen-based material in an aqueous medium at an acidic pH to react at least a portion of the collagen carboxyl groups with the epoxy functionalized crosslinking agent to form crosslinked collagen-based material comprising residual collagen carboxyl groups. Preferably, the residual collagen carboxyl groups are reacted with the collagen amine groups to form zero-length crosslinks.

Another method for crosslinking collagen-based material having collagen amine groups and collagen carboxyl groups is provided. The method comprises: combining a diepoxy crosslinking agent with the collagen-based material in an aqueous medium at an acidic pH to react at least a portion of the collagen carboxyl groups with the diepoxy crosslinking agent to form crosslinked collagen-based material comprising residual collagen carboxyl groups; and reacting a portion of the residual collagen carboxyl groups with an activating agent in the presence of a stabilizing agent to form activated carboxyl groups capable of reacting with carboxyl amine groups.

Preferably, the activating agent is selected from the group of a carbodiimide, an azide, 1,1'-carbonyldiimidazole, N,N'-disuccinimidyl carbonate, 2-ethoxy-1-ethoxycarbonyl-1,2-dihydroquinoline, and 1,2-benzisoxazol-3-yl-diphenyl phosphate, N-ethyl-5-phenylisoxazolium-s'-sulfonate, and mixtures thereof. A particularly preferred activating agent is the partially water soluble carbodiimide, 1-ethyl-3-(3-dimethylaminopropyl) carbodiimide.HCl. To enhance the stability of the reactive intermediate, particularly when a carbodiimide is the activating agent, the step of activating preferably comprises reacting the collagen carboxyl groups with an activating agent in the presence of a stabilizing agent, such as N-hydroxysuccinimide The epoxy functionalized crosslinking agent used in the method of the present invention is preferably a polyepoxy hydrophilic crosslinking agent, and more preferably, a diepoxide. A preferred class of such crosslinking agents is polyol polyglycidylethers, such as, but not limited to, glycol diglycidyl ether, glycerol diglycidyl ether, glycerol triglycidyl ether, and butanediol diglycidyl ether. A particularly preferred diepoxy (i.e., diepoxide) crosslinking agent has the following formula:

wherein R may be any substituent that does not interfere with the crosslinking process and/or diminish the solubility of the crosslinking agent in aqueous solutions; and wherein n=1–6, preferably n=1–4.

Furthermore such crosslinking agents may be selected from the group of polyglycidylether-functional molecules of polyethlyeneglycol, polypropyleneglycol, and polyethylene-propyleneglycol, for which the diglycidylether derivative can be represented by the following general formula:

wherein x+z=0–70 and y=0–90.

The present invention also provides a bioprosthetic device comprising collagen-based material crosslinked with an epoxy functionalized crosslinking agent through a portion of the collagen carboxyl groups and further crosslinked through collagen carboxyl groups directly bonded to collagen amine groups.

DETAILED DESCRIPTION OF THE INVENTION

The present invention provides methods for making a bioprosthetic device, which is derived in whole or in part from natural tissues that contain collagen-based materials, and the resultant products. Such bioprosthetic devices include, for example, heart valves and other heart components, vascular replacements or grafts, urinary tract and bladder replacements, bowel and tissue resections, tendon replacements, and the like. Such collagen-based materials include whole tissue (i.e., tissue containing collagen and noncollagenous substances or cells), only the collagen matrix without the noncollagenous substances, and purified fibrous collagen. Typically, and preferably, however, whole tissues are used in making bioprosthetic implants.

Specifically, the present invention provides a method for making a bioprosthetic device made of collagen-based material, such as a heart valve, by crosslinking the collagen-based material primarily through collagen carboxyl groups with an epoxy functionalized crosslinking agent. Although epoxy compounds are also reactive toward amine groups, particularly under basic conditions, the pH of the crosslinking reaction of the present invention is controlled such that reaction of the epoxy compounds with collagen carboxyl groups is enhanced relative to reaction with amine groups. That is, although it is known to crosslink collagen-based materials (often simply referred to herein as "collagen") using epoxy compounds, such crosslinking typically occurs at basic pH, which results in crosslinking via the collagen amine groups. In contrast, the methods of the present invention involve crosslinking collagen-based materials with epoxy compounds at acidic pH, which results in crosslinking primarily via the collagen carboxyl groups. This allows for the collagen amine groups to be available for blocking reactions, additional crosslinking reactions, or coupling of bioactive molecules.

A preferred method of the present invention involves first combining the collagen-based material with one or more epoxy functionalized crosslinking agents at an acidic pH to crosslink the collagen through a portion of the collagen carboxyl groups, and subsequently combining this partially crosslinked collagen with an activating agent that activates at least a portion of the remaining free carboxyl groups (i.e., the residual carboxyl groups) toward collagen amine groups to further crosslink the collagen through a "zero-length" crosslink (i.e., reaction of activated carboxyl groups of collagen with free amine groups of collagen). This is unexpected because a large number of zero-length crosslinks makes collagenous materials stiff and brittle, which is typically in contrast to the desired mechanical properties of a bioprosthetic device. By combining these two types of crosslinking, however, this method balances the amount of zero-length crosslinks and provides significant advantage, particularly with respect to the engineering of desired properties.

Crosslinking via the carboxyl groups using an epoxy functionalized crosslinking agent provides a number of advantages over crosslinking via the amine groups. First, collagen-based materials crosslinked via collagen carboxyl groups typically have superior mechanical properties. For example, such material feels very pliable and loose after lyophilization, as compared to collagen-based materials crosslinked with an epoxy functionalized crosslinking agent via collagen amine groups, which are more rigid and condensed. When compared to materials crosslinked with epoxy functionalized crosslinking agents via amine groups, mechanical testing (uni-directional) of materials crosslinked with epoxy functionalized crosslinking agents via carboxyl groups shows a generally higher ultimate tensile strength, a generally higher percentage of elongation at break, and a generally higher force necessary to produce a specific elongation. This latter observation is particularly significant because it demonstrates that with increasing strain, collagen-based materials crosslinked with epoxy functionalized crosslinking agents via carboxyl groups become more resistant toward further elongation. This is similar to the mechanical behavior of vascular tissue.

Second, crosslinking with an epoxy functionalized crosslinking agent via the carboxyl groups retains the collagen amine groups free for further chemical modification. Such modification can include, for example, blocking reactions, additional crosslinking reactions, or coupling of bioactive molecules.

Blocking of the collagen free amine groups may significantly reduce the antigenicity of the material as does glutaraldehyde crosslinking, which crosslinks via the collagen amine groups. Blocking can occur prior to, or subsequent to, epoxy crosslinking via the collagen carboxyl groups. A wide variety of blocking techniques can be used according to the present invention.

The collagen free amine groups can be used to increase the crosslink density, either between two amine groups or between a free amine group and a residual carboxyl group. Such additional crosslinking allows for further engineering of the mechanical properties of the material. It also provides enhanced resistance towards biodegradation of the collagen-based material. A wide variety of known crosslinking techniques can be used according to the present invention. Preferably, however, direct crosslinking between residual collagen carboxyl groups and free collagen amine groups to form zero-length crosslinks is promoted through the use of carboxyl group activating agents, such as carbodiimide.

The collagen free amine groups can also be used to couple bioactive molecules into the collagen matrix. As a result, a material can be produced that actively participates in the host-material interaction, thereby enhancing the acceptance and performance of the material. A wide variety of known biomolecules can be used according to the present invention. Examples include, but are not limited to, angiogenic factors, growth factors, antimicrobial agents, antithrombotic agents, and anticalcification agents.

The collagen carboxyl groups are reacted with a polyfunctional, preferably, a bifunctional, epoxy functionalized crosslinking agent to partially crosslink the collagen-based material. It is believed that the introduction of such crosslinking agents allows the formation of crosslinks that not only bridge the distance between two adjacent collagen fibers or fiber bundles, but also introduce extra flexibility into the whole matrix. The epoxy functionalized molecules are of largely hydrophilic nature, soluble in aqueous solutions, with the reactive moieties preferably located at the respective ends of the longest molecular chain. They may include straight-chain or branched-chain groups with a variety of substitutions possible, although substitutions in the chain should not interfere with the crosslinking process and/or diminish the solubility of the crosslinking agent in aqueous solutions. Hydrophilicity of the epoxy functionalized crosslinking agent is believed to be advantageous as this can effect infiltration and diffusion of tissue fluid through the bioprosthetic matrix.

Suitable hydrophilic epoxy functionalized crosslinking agents include, for example, polyol polyglycidyl ethers, such as, but not limited to, glycol diglycidyl ether, glycerol diglycidyl ether, glycerol triglycidyl ether, and butanediglycidyl ether. Preferably, the epoxy functionalized crosslinking agent is a diepoxy crosslinking agent. A preferred class of hydrophilic diepoxy crosslinking agents include those of the following general formula:

wherein R may be any substituent that does not interfere with the crosslinking process and/or diminish the solubility of the crosslinking agent in aqueous solutions; and wherein n=1–6, preferably n=1–4.

Furthermore such crosslinking agents may be selected from the group of polyglycidylether-functional molecules of polyethyleneglycol, polypropyleneglycol, and polyethylenepropyleneglycol, for which the diglycidylether derivative can be represented by the following general formula:

wherein x+z=0–70 and y=0–90. Such crosslinking agents are commercially available from a variety of sources, such as Fluka Chemical, Buchs, Switzerland.

The use of hydrophilic epoxy functionalized crosslinking agents can advantageously render the crosslinked material hydrophilic. As stated above, this is believed to effect proper infiltration and diffusion of tissue fluid through the biopros-thetic matrix. This provides a supply of oxygen, nutritive substances, and electrolytes into the tissue, as well as drainage of metabolized substances from the tissue. As a result, the growth of capillary blood vessels and cells will be promoted, and consequently a good healing response to the implanted material.

Additionally, it is believed that crosslinking agents having a highly flexible, long-chain structure will effect crosslinking in between adjacent fibers and fiber bundles, which will have a beneficial effect on the mechanical properties of the resultant crosslinked material.

The epoxy functionalized crosslinking agent(s) are used in amounts effective to crosslink a desired number of the carboxyl groups. Preferably, this amount involves a molar ratio of the epoxy functionalized crosslinking agent(s) relative to the number of activated carboxylic acid groups of about 1:1 to about 25:1, more preferably about 4:1 to about 20:1, and most preferably about 8:1 to about 16:1.

The crosslinking reaction is carried out in an acidic aqueous solution. Under acidic conditions, the epoxide groups are protonated, which are subject to nucleophilic attack by carboxylate anions, thereby forming ester linkages. Preferably, the solution has a pH of about 3 to about 7, more preferably, about 4 to about 6.5, and most preferably, about 4.5 to about 6. The temperature of this reaction should be below that at which the collagen-based material is denatured. Thus, although increased temperatures do increase reaction rates, effective crosslinking takes a matter of days. The maximum value of the shrinkage temperature ($T_s$), a measure for the efficacy of crosslinking, hardly changes with reaction temperature. Therefore, reactions are preferably performed at room temperature (i.e., about 20–25° C.), and more preferably, at about 21° C.

After the collagen-based material is crosslinked with epoxy compounds through collagen carboxyl groups, the free (i.e., residual) collagen amine groups can be crosslinked. This can be done by first activating at least a portion of the residual collagen carboxyl groups (i.e., those collagen carboxyl groups unreacted with epoxy crosslinking agent molecules). These residual carboxyl groups can be activated by a variety of methods. Carbodiimide s reagents are well-known activating agents and traditionally most often used. Reaction between a carboxyl group and a carbodiimide yields the reactive intermediate O-acylisourea; this intermediate is prone to a nucleophilic attack in a subsequent step. In addition, an intramolecular rearrangement reaction in which the O-acylisourea rearranges to the much more stable, but much less reactive, N-acylurea may happen. Under typical reaction conditions, the half-life of this intermediate is in the range of seconds to minutes.

The reactive O-acylisourea can be stabilized through the use of a succinimide or other stabilizing reagents. Using a stabilizing agent in addition to the activating agent can increase the half-life of the O-acylisourea to 30–40 minutes under typical reaction conditions. Also, significantly, the intramolecular rearrangement reaction is suppressed. Typically, these stabilizing agents themselves are also capable of activating the carboxyl groups, although much less effectively than when combined with carbodiimides.

Examples of activating agents other than carbodiimide include, but are not limited to, those typically used in peptide synthesis. Examples include 1,1'-carbonyldiimidazole (CDI), N,N'-disuccinimidyl carbonate (DSC), 2-ethoxy-1-ethoxycarbonyl-1,2-dihydroquinoline (EEDQ), and 1,2-benzisoxazol-3-yl-diphenyl phosphate (BDP), and N-ethyl-5-phenylisoxazolium-s'-sulfonate (Woodwards Reagent K). Such activating agents are at least partially soluble in water. Although activating agents that are not at least partially water soluble, such as azides (e.g., diphenylphophorylazide as disclosed in U.S. Pat. No. 5,264,551 (Petite et al.)), can be used in the method of the present invention, they are not particularly desirable. Mixtures of activating agents can be used.

Preferably, the residual collagen carboxyl groups are activated by reaction with a carbodiimide that is at least partially soluble in water. A particularly preferred water-soluble carbodiimide suitable for use in the present invention is 1-ethyl-3-(3-dimethylaminopropyl) carbodiimide-.HCl (EDC). Other suitable carbodiimides include, for example, cyanamide and N,N'-dicyclohexylcarbodiimide (DCC), N,N'-diisopropylcarbodiimide (DIC), and 1-cyclohexyl-3-(2-morpholinoethyl) carbodiimide metho-p-toluenesulfonate (CMC).

As stated above, when a carbodiimide is used to activate the carboxyl groups, O-acylisourea groups are formed that can rearrange to less reactive N-acylurea groups. The addition of N-hydroxysuccinimide (NHS) is known to decrease this tendency for rearrangement. Other stabilizing agents, such as N-hydroxybenzotriazole (HOBt), N-hydroxy-5-norbornene-endo-2,3-dicarboximide (HONB), 4-dimethylaminopyridine (DMAP), and the sulfo-derivative of N-hydroxysuccinimide, are also capable of accomplishing this. Mixtures of such stabilizing agents can be used. In particularly preferred methods of the present invention, the collagen carboxyl groups are activated using a mixture of a carbodiimide (preferably, EDC) and NHS.

Various mixtures of the above activating agents and optional stabilizing agents can be used in the methods of the present invention. The activating agent or agents are used in amounts effective to activate at least a portion, and preferably, a majority (i.e., greater than about 50%), of the residual collagen carboxyl groups. More preferably, the activating agent or agents are used in a molar excess relative to the number of residual collagen carboxyl groups. The stabilizing agent or agents are used in amounts effective to stabilize a majority of the activated carboxyl groups. Preferably, the stabilizing agent or agents are used in an amount of at least a level that equals the number of residual collagen carboxyl groups. More preferably, the stabilizing agent or agents are used in a molar excess relative to the number of residual collagen carboxyl groups, but preferably not exceeding the molar level of the activating agent or agents.

The activating reaction is preferably carried out in an aqueous solution, more preferably, a buffered aqueous solution having a pH of about 4 to about 9 (preferably, about 5 to about 7, and more preferably, about 5 to about 6).

Although using a carbodiimide crosslinking technique to form zero-length crosslinks is particularly preferred subsequent to crosslinking collagen-based materials with the epoxy functionalized crosslinking agents, other crosslinking techniques can be used. For example, dicarboxylic acid spacers can be used during the carbodiimide crosslinking technique. These spacers preferably are of hydrophilic nature, such as dicarboxylic acid functional polyethyleneglycol, polypropyleneglycol, or polyethyleneglycol-polypropyleneglycol polymers. The use of these spacers during the carbodiimide crosslinking would provoke introduction of crosslinks between the free amine groups of collagen. It is also possible to use spacers that have functional groups able to directly couple to the free amine groups of collagen, obviating the need for using carbodiimides. Examples are dialdehyde functional spacers or disuccinimidyl functional spacers. Again, these spacers preferably are of hydrophilic nature, such as dialdehyde functional polyethyleneglycol, or the di-succinimidyl derivative of polypropyleneglycol.

The free amine groups of the partially crosslinked collagen-based materials can be blocked by various types of chemical reagents if desired. Furthermore, such blocking techniques could also be used before a portion of the carboxyl groups are reacted with the epoxy compounds (i.e., before crosslinking with the epoxy functionalized crosslinker). The four major types of reactions through which blocking of free amines can be achieved are: (1) acylation reaction; (2) amination reaction, preferably involving reductive amination using aldehydes or ketones; (3) amination reaction using epoxides; and (4) amination reaction with sulphonyl or sulphonic acid derivatives. Preferably, small blocking agents, i.e., those having about two to six carbon atoms in length, are used in order to prevent significant disruption of the native triple helix structure of the collagen. Although such reactions involving the use of small blocking agents are preferred, biologically active compounds can also be used to block the free amine groups.

There are numerous acylating agents for use in blocking the amine groups using the acylation reaction. Of particular importance are the isocyanates, isothiocyanates, acid halides, acid anhydrides, activated esters (i.e., those having a good leaving group that is easily released upon reaction with an amine) such as N-hydroxysuccinimide ester, and imidoesters. Preferred acylating agents include, but are not limited to: N-hydroxy succinimide esters (NHS), such as acetic acid N-hydroxysuccinimide ester, sulfo-NHS-acetate, and propionic acid N-hydroxysuccinimide ester; p-nitrophenyl esters such as p-nitrophenyl formate, p-nitrophenyl acetate, and p-nitrophenyl butyrate; 1-acetylimidazole; and citraconic anhydride (reversible blocker).

There are numerous aminating agents (e.g., alkylating agents) for use in blocking the amine groups using the amination reaction. Particularly preferred are aldehydes and ketones. Reaction of a free amine with an aldehyde or ketone yields an imine (or Schiff base) that is quite stable (particularly when an aryl group is present). If necessary, however, the formed imine can be further stabilized through reduction with reducing agents like sodium cyanoborohydride, sodium borohydride, or borane reagents such as dimethylamine borane, trimethylamine borane or morpholine borane.

Aldehydes are preferred aminating agents because ketones generally react more slowly and often require higher temperatures and longer reaction times. A wide variety of aldehydes can be used. Preferably, the aldehydes are monofunctional aldehydes. Examples of monofunctional aldehydes include, but are not limited to, propanal, butanal, and hexanal (caproaldehyde).

Monofunctional epoxides can be also used as the aminating agent to block the amine groups. A monofunctional epoxide forms a secondary amine; however, it is anticipated that such groups will be sufficiently sterically hindered that, under typical reaction conditions, crosslinking will not occur. Suitable monofunctional epoxides include, for example, iso-propylglycidylether and n-butylglycidylether.

Sulphonyl or sulphonic acid derivatives are another group of aminating agents that may be used to block free amine groups. Preferably, the sulphonyl or sulphonic acid derivative is monofunctional. An exemplary reagent is 2,4,6-trinitrobenzenesulfonic acid, for example.

A wide variety of biologically active derivatives of such compounds (i.e., those containing an appropriate reactive moiety such as an ester, aldehyde, or ketone, for example) can be used to block the free amine groups. As a result, desirable biological functions can be included into the collagenous matrix that may improve biocompatibility and overall performance. An example is aldehyde-functional heparin, obtained either through periodate oxidation (periodate-heparin) or nitrous acid degradation (NAD-heparin).

A mixture of the above blocking agents can be used in the methods of the present invention. The blocking agent (or mixture of blocking agents) is used in an amount effective to block at least a portion, preferably, a majority (i.e., greater than about 50%), of the free amine groups. More preferably, the blocking agent(s) is used in a significant molar excess relative to the number of free amine groups.

The blocking reaction is preferably carried out in an aqueous solution, and more preferably, in a buffered aqueous solution having a pH of about 6 to about 7.

Preferably, such blocking agents are capable of blocking at least about 75% of the free collagen amine groups, more preferably, at least about 80%, and most preferably, at least about 90%, of the free collagen amine groups. Typically, blocking the amine groups provides improvement in the biocompatibility of the collagen-based material because free amine groups have been suggested to be involved in the immune response.

Crosslinking of collagen-based materials according to the methods of the present invention yield a material with a generally high degree of crosslinking and a generally high resistance toward enzymatic digestion, while the material maintains a relatively high degree of flexibility without substantial stiffening over time. This material is also preferably highly hydrophilic, which is believed to increase the biocompatibility of the material. The great reduction in free amine groups also contributes to a better biocompatibility by lowering the antigenic potential of the material. As discussed before, the biocompatibility of this material can also be improved by blocking the amine groups with appropriate biologically active molecules, such as for instance, the very blood compatible molecule heparin, instead of using small biologically nonactive molecules. These properties make the methods according to the present invention particularly suitable for crosslinking of cardiovascular bioprostheses, such as heart valves and vascular grafts.

The invention will be further described by reference to the following detailed examples. These examples are offered to further illustrate the various specific and illustrative embodiments and techniques. It should be understood, however, that many variations and modifications may be made while remaining within the scope of the present invention.

EXPERIMENTAL EXAMPLES

Materials and Methods

Preparation of DSC. Dermal sheep collagen (DSC) was used as a model for porcine aortic heart valves because this material provides a tissue matrix-like structure, while being a pure collagen material. The latter allows for more precise evaluation and characterization of the material after having the crosslinking process employed, and as such a better understanding of the relationship between the crosslinking chemistry and consequent material behavior, mechanically as well as biologically, is obtained. The material was obtained from the Zuid-Nederlandse Zeemlederfabriek (Oosterhout, The Netherlands). DSC was prepared in a process in which the skin first was depilated and immersed in a lime-sodium sulfide solution to remove the epidermis. Non-collagenous substances were removed using proteolytic enzymes whereafter the skin was split to obtain the dermal layer. The remaining fibrous collagen network was extensively washed with water (4 times), with acetone (2 times), and with deionized water (2 times) before freeze-drying. This procedure yielded noncrosslinked DSC (NDSC).

Crosslinking with a Diepoxide. A sheet of 1 gram (g) of NDSC was immersed in 100 ml of a buffered solution containing 4% (by weight) 1,4-butanediol diglycidyl ether (BDDGE; Fluka Chemical, Buchs, Switzerland). The solution was buffered with either 0.05 Molar (M) 2-(N-morpholino)ethanesulfonic acid (MES; Merck, Darmstadt, Germany) for pH 4.5 or with 0.025 M $Na_2B_4O_7.10H_2O$ (sodium tetraborate decahydrate) for pH 9.0. The reaction was allowed to proceed for 7 days at room temperature. After reaction, the samples were rinsed with tap water and then with deionized water before freeze-drying. This procedure yielded DSC crosslinked with BDDGE at pH 4.5 (BD45) or pH 9.0 (BD90).

Crosslinking with EDC and NHS. A sheet of 1 g of BD45 was immersed in 100 ml of a 0.05 M MES buffered solution (pH=5.5) containing 1.15 g 1-ethyl-3-(3-dimethylaminopropyl)carbodiimide.HCl (EDC; Aldrich, Zwijndrecht, The Netherlands), and 0.276 g N-hydroxysuccinimide (NHS; Aldrich, Zwijndrecht, The Netherlands). The reaction was allowed to proceed for 2 hours at room temperature. After reaction, the DSC was washed with 0.1 M $NaH_2PO_4$ for 2 hours and then with deionized water before freeze-drying. This procedure yielded DSC crosslinked with BDDGE at pH 4.5 and zero-length crosslinks (BD45EN).

Crosslinking with Glutaraldehyde. A sheet of 1 g of NDSC was immersed in 100 ml of a 0.5 wt-% glutaraldehyde solution (GA distilled, boiling point 85–86° C., 18 mm Hg) in a phosphate buffer (0.054 M Na2HPO4, 0.13 M $NaH_2PO_4$, pH 7.4) for 1 hour at room temperature. After crosslinking, the sample was rinsed with tap water for 15 minutes, washed with 4 M NaCl (2× for 30 minutes each) and deionized water (4× for 30 minutes each) before freeze-drying. This procedure yielded glutaraldehyde crosslinked DSC (GDSC).

Blocking of free amine groups—acylation process. The acylating agent acetic acid N-hydroxysuccinimide ester (HAc-NHS; Sigma, Zwijndrecht, The Netherlands) was used to block the free amine groups of the collagen crosslinked with BDDGE at pH 4.5. A sheet of 1 gram (g) of BD45 was immersed in a 0.05 M MES (Fluka, Buchs, Switzerland) buffered solution (pH=6.8) containing 2.6 g HAc-NHS; molar ratio of HAc-NHS to free amine groups of collagen was approximately 25:1. The reaction was allowed to proceed for about 16 hours at room temperature. After reaction, the DSC was washed 3 times for 15 minutes each with deionized water and freeze-dried. This procedure yielded HAc-NHS blocked DSC crosslinked with BDDGE at pH 4.5 (BD45HAC).

Free amine group content. The primary amine group content of crosslinked DSC samples, expressed as the number of free amine groups present per 1000 amino acids (n/1000) or as a percentage of the NDSC (%), was determined using a 2,4,6-trinitrobenzenesulfonic acid (TNBS; 1.0 M solution in water, Fluka, Buchs, Switzerland) colorimetric assay. To a sample of 2–4 milligrams (mg) of DSC was added 1 ml of a 4% (weight/volume) aqueous $NaHCO_3$ (pH 9.0; Aldrich, Bornem, Belgium) solution and 1 ml of a freshly prepared 0.5% (weight/volume) aqueous TNBS solution was added. After reaction for 2 hours at 40° C., 3.0 ml of 6 M HCl (Merck, Darmstadt, Germany) was added and the temperature was raised to 60° C. When complete solubilization of DSC was achieved (approximately 90 minutes after addition of HCl), the resulting solution was diluted with 15 ml of deionized water and the absorbance was measured on a Hewlett-Packard HP8452A UV/VIS spectrophotometer at a wavelength of 345 nm. A control was prepared applying the same procedure except that HCl was added before the addition of TNBS. The free amine group content was calculated using a molar absorption coefficient of 14600 $l \cdot mol^{-1} cm^{-1}$ for trinitrophenyl lysine [Wang C. L., et al., *Biochim. Biophys. Acta*, 544, 555–567, (1978)].

Degree of crosslinking. Differential scanning calorimetry was used to study the efficacy of the various crosslinking procedures. Heating (crosslinked) collagen will induce a structural transition of the native triple helical structure at a certain temperature dependent on the nature and degree of crosslinking. Introduction of covalent crosslinks will increase the stability of the triple helix, thus increasing the denaturation temperature. The temperature at which denaturation takes place is also often referred to as shrinkage temperature $T_s$), as shrinkage is the macroscopic manifestation of the transformation of the native triple helix structure to the random coil configuration.

Treated and nontreated collagen samples were characterized using a Perkin Elmer DSC7 series. In a typical run 5–8 milligrams (mg) collagen was placed into a 50 microliter (μl) aluminum sample pan (2 bar maximum internal pressure), after which 5 μl/mg 0.1 M phosphate buffer (pH=6.88; 0.05 M $Na_2HPO_4$, 0.05 M $NaH_2PO_4$-both Merck, Darmstadt, Germany) was added to hydrate the collagen. The sample pan was covered with an appropriate cover and the whole was crimp pressed. An empty sample pan was used as the reference. Typically, a run was started at 20° C. (load temperature); after 2 minutes, samples were heated to 100° C., applying a heating rate of 2° C./minute. Device software was used to optimize data collection, and to calculate typical properties.

Pronase digestion assay. The digestion of treated and nontreated DSC was performed by immersing a collagen disc of 15 mg in 5 ml of a pre-warmed (T=37° C.) solution of 0.1 M tris(hydroxymethyl)aminomethane hydrochloride (TRIS-HCl, pH 7.4; Aldrich, Bornem, Belgium) containing 5 mM $CaCl_2$ (Janssen Chimica, Geel, Belgium), 0.05 mg/ml $NaN_3$ (Merck, Darmstadt, Germany) and 20 U/ml pronase (from *Streptomyces grisseus*, 7000 U/g lyophilizate, Boehringer Mannheim GmbH, Germany). Degradation was discontinued at the desired time interval by the addition of 0.5 ml 0.25 M EDTA (Janssen Chimica, Geel, Belgium), after which the solutions were cooled on ice. The pronase solution was decanted after which the disc was washed 3 times for 15 minutes in 0.1 M TRIS-HCl buffer (pH=7.4), 3 times for 15 minutes in deionized water, and freeze-dried. The percent remaining weight (i.e., change in weight as a percentage of the initial weight) was determined gravimetrically and used as a measure for the resistance towards enzymatic digestion.

Collagenase digestion assay. The digestion of treated and nontreated DSC was performed by immersing a collagen disc of 6–10 mg in 0.5 ml of a pre-warmed (T=37° C.) solution of 0.1 M TRIS-HCl buffer (pH 7.4; Aldrich, Bornem, Belgium) containing 5 mM $CaCl_2$ (Janssen Chimica, Geel, Belgium), 0.05 mg/ml $NaN_3$ (Merck, Darmstadt, Germany). After 1 hour, 0.5 ml of a pre-warmed (T=37° C.) solution of 0.1 M TRIS-HCl buffer (pH 7.4) and 20 U/ml pronase collagenase (from Clostridium Histolyticum, 315 U/mg, Sigma, St. Louis, Mo.) was added. Degradation was discontinued at the desired time interval by the addition of 0.1 ml 0.25 M EDTA (Titriplex III, Pa., Merck, Darmstadt, Germany), after which the solutions were cooled on ice. The collagenase solution was decanted after which the disc was washed 3 times for 15 minutes in 0.1 M TRIS-HCl buffer (pH=7.4), 3 times for 15 minutes in deionized water, and freeze-dried. The percent remaining weight (i.e., change in weight as a percentage of the initial weight) was determined gravimetrically and used as a measure for the resistance towards enzymatic digestion.

Mechanical Properties. Stress-strain curves of DSC samples were determined by uniaxial measurements using a Zwick mechanical tester. Because of variations in the mechanical properties of different parts of the sheep skin, only samples (crosslinked, modified, or noncrosslinked) were taken from the IUP/2 sampling area (IUP/2, *J. Soc. Leather Trades' Chemists* 44, (1960)) parallel to the backbone. Tensile bars (40.0 mm×4.0 mm×1.4 mm) were cut using a dumb-bell shaped knife and were hydrated for at least one hour in PBS at room temperature. The thickness of the samples was measured in triplicate using a spring-loaded type micrometer (Mitutoyo, Tokyo, Japan). An initial gauge length of 10 mm was used and a crosshead speed of 5 mm/minute was applied until rupture of the test specimen occurred. A preload of 0.05 N was applied to prestretch the specimen before the real measurement. The tensile strength, the elongation at alignment, the elongation at break, the low strain modulus and the high strain modulus of the sample were calculated from five independent measurements.

Results

Figure 1:
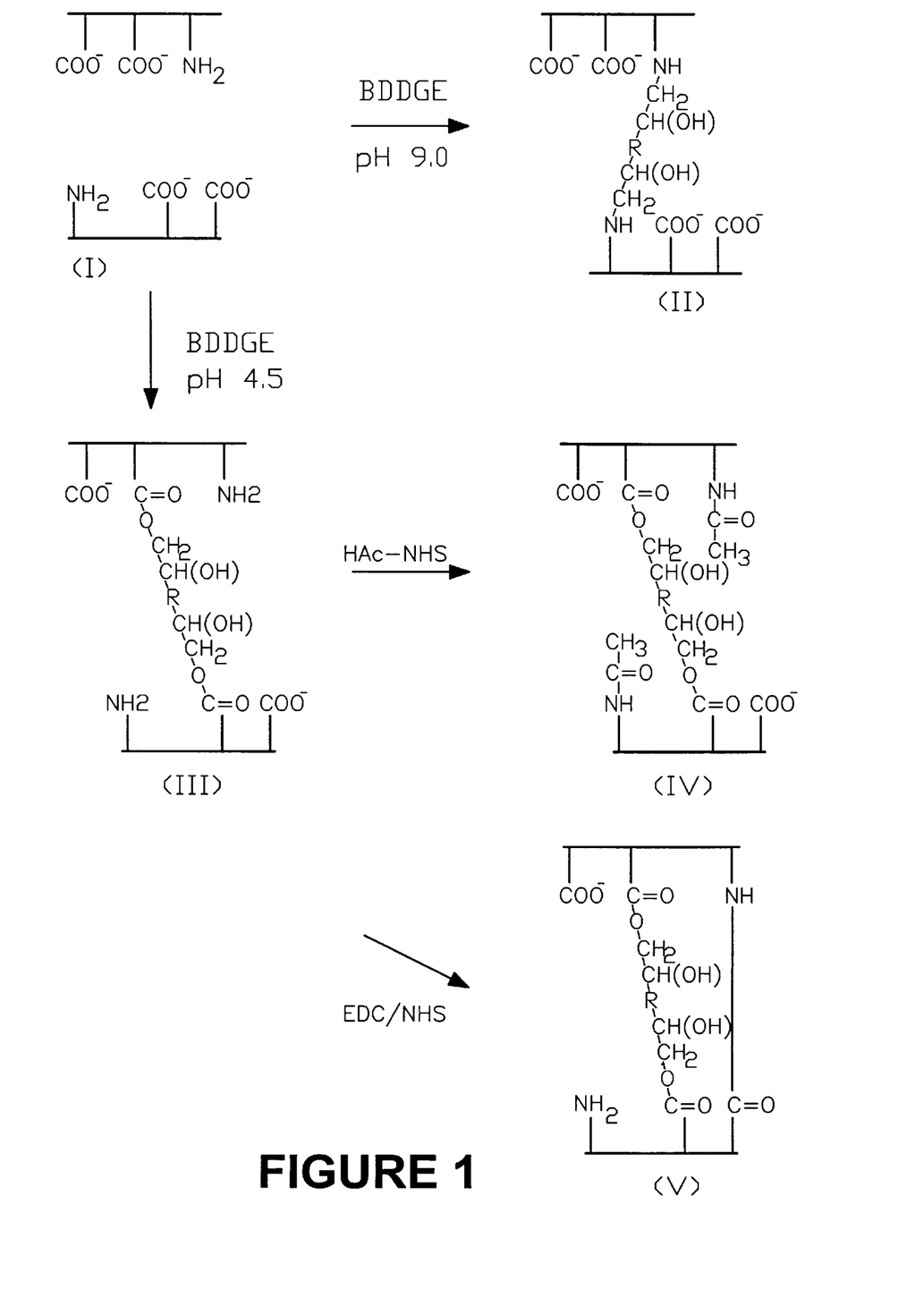
FIG. 1 is a schematic representation depicting an overview of possible crosslinking techniques disclosed in the presented invention.

Crosslinking. Referring to FIG. 1, crosslinking of dermal sheep collagen (I) using a diglycidyl ether involves reaction between two amine residues (lysine) if alkaline conditions were used (II) or reaction between two carboxylic acid residues (aspartic or glutamic acid) if crosslinking was performed under acidic conditions (III). It might be possible that only one side of the BDDGE molecule has reacted leading to a modified amine group and in introduction of a pendant epoxide group. Acetylation of the free amine groups of (III) lead to structure (IV). No additional crosslinks were formed during this reaction.

EDC/NHS crosslinking of (III) results in additional crosslinks. EDC/NHS crosslinking involves the activation of the residual carboxyl groups with EDC to give an O-acylisourea group. In the presence of NHS, this group can be converted to NHS activated carboxylic acid group, which is very reactive towards amine groups under formation of a peptide bond (zero-length crosslinks).

The shrinkage temperature ($T_s$) and the percentage of free amines were determined to get an indication of the degree of reaction after the different crosslink procedures.

TABLE 1

Initial Properties

| Material | Shrinkage Temperature (° C.) | Free Amine Groups [%] |
|---|---|---|
| N-DSC | 45.9 ± 0.8 | 100 ± 3.0 |
| GDSC | 69.2 ± 0.5 | 38.3 ± 1.5 |
| BD45 | 63.5 ± 3.5 | 87.4 ± 1.0 |
| BD90 | 67.0 ± 4.0 | 46.5 ± 2.5 |
| BD45Hac | 61.7 ± 3.5 | 33.6 ± 9.0 |
| BD45EN | 81.0 ± 1.0 | 56.6 ± 8.0 |

N-DSC contained 31 ± 1 amine residues per 1000 amino acids

All crosslinked materials show a considerable increase of the shrinkage temperature (16–36° C.) indicating that the collagen was crosslinked. It is clear that different values of $T_s$ were obtained depending on the crosslinked procedure. GA crosslinking involves reaction with the free amine groups, leading to a very complex reaction. BDDGE crosslinking led to an increase of $T_s$ in combination with a decrease in free amine groups. About the same degree of crosslinking as GA can be obtained if crosslinking was performed at alkaline conditions (BD90). Acidic crosslinking resulted in a slightly lower $T_s$ and in only a small decrease of amines (12%) indicating that crosslinking mainly occur via the carboxyl groups.

Acetylation of the residual amine groups results in a steep decrease in amines (87% to 33%) and in a slight decrease in $T_s$. Finally, a second crosslinking step using a water-soluble carbodiimide (EDC) in combination with NHS showed a very high $T_s$ combined with a moderate amount of amine group left (56%).

DSC measurements of the different materials were performed in order to get more information about the transition and its thermodynamics as a function of the crosslink procedure.

TABLE 2

The Thermodynamics of the Shrinkage Transition of DSC

| Material | $T_{peak}$ [° C.] | $\Delta T$ [° C.] | $\Delta H$ [J/g tissue] | Peak Shape |
|---|---|---|---|---|
| N-DSC | 39.4 | 12.3 | 15.1 | non-symmetric |
| GDSC | 64.8 | 10.0 | 10.7 | non-symmetric |
| BD45 | 69.6 | 4.0 | 16.9 | symmetric |
| BD90 | 72.8 | 8.8 | 7.6 | non-symmetric |
| BD45HAc | 66.7 | 5.6 | 16.6 | symmetric |
| BD45EN | 77.2 | 8.5 | 19.3 | symmetric |

Table 2 shows the calorimetric results of the (non) crosslinked DSC sheets. Crosslinking will not only increase the $T_s$, but will show a narrower transition and a change in the transition enthalpy. Acidic crosslinking of DSC resulted in a symmetrical shaped narrow transition peak indicating that the crosslinks were homogeneously distributed in the material.

Macroscopic appearance. There were some apparent differences in macroscopic appearance. These were collected in the next table.

TABLE 3

Macroscopic Properties of (Non) Crosslinked DSC.

| Material | Appearance | Hydrolysis Time (min) in 6 M HCl at 60° C. |
|---|---|---|
| N-DSC | white, soft, loose | 10–15 |
| ODSC | yellow, stiff, compact | 45–75 |
| BD45 | white, loose, very soft | 30–45 |
| BD90 | white, stiff, moderately compact | 60–90 |
| BD45Hac | white, moderately loose, soft | 30–45 |
| BD45BN | white, loose, soft | 60–100 |

This table shows that crosslinking via the carboxyl groups (BD45) resulted in completely different macroscopic properties, soft and loose structure, compared to amine crosslinked materials (GA, BD90), which showed a rather stiff compact structure.

The rate of hydrolysis of BD45 is much higher than GA and BD90, because of the hydrolytically unstable ester linkages. Nevertheless, a second additional crosslinking step of BD45 enhanced the stability and maintained the soft and loose structure.

Figure 2:
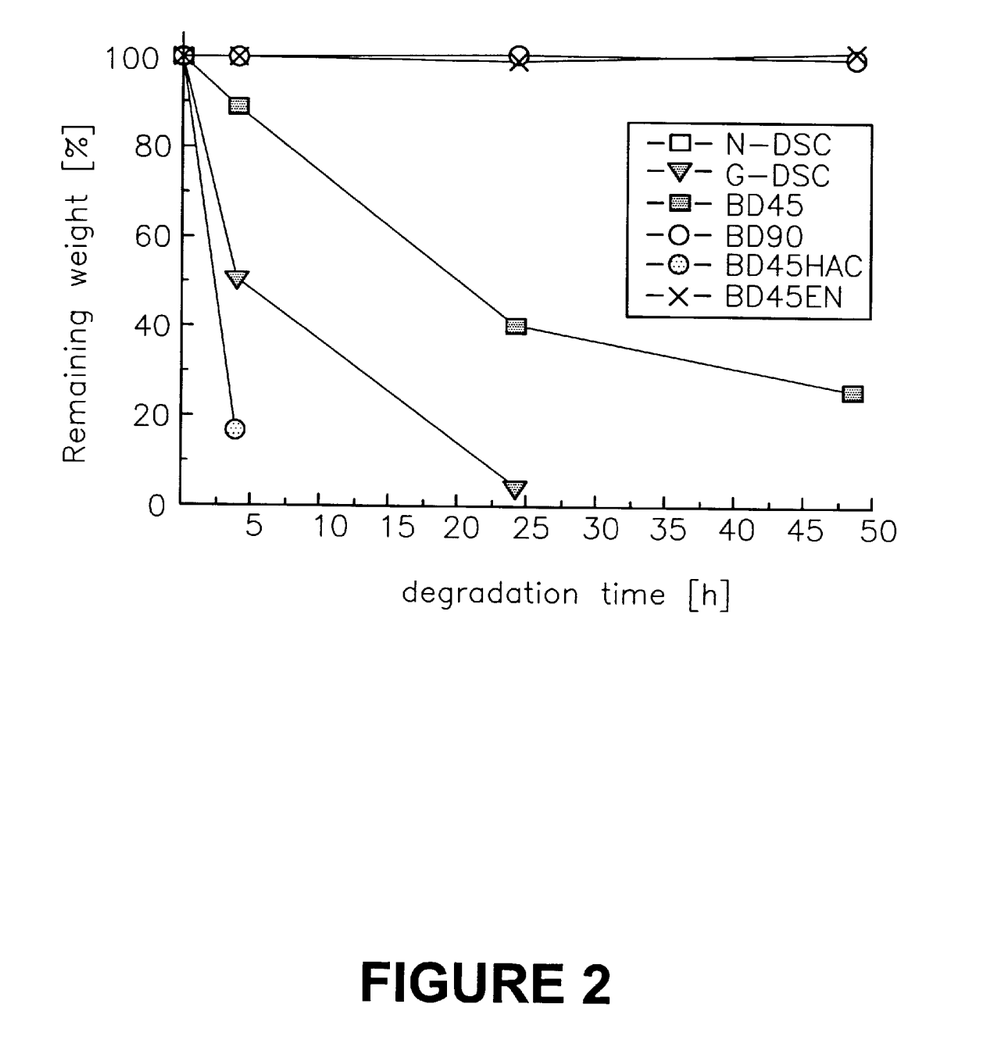
FIG. 2 is a graph of weight change (in % of initial weight) as a function of pronase degradation time (in hours).
Figure 3:
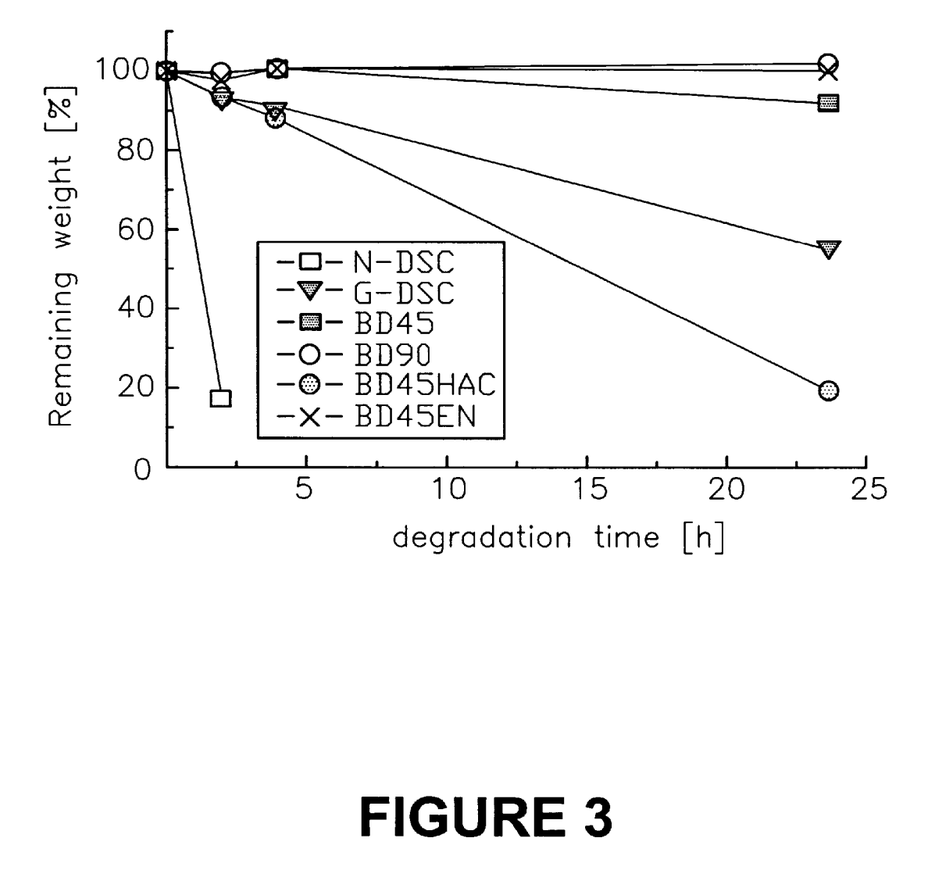
FIG. 3 is a graph of weight change (in % of initial weight) as a function of collagenase degradation time (in hours).

Degradation Studies. N-DSC was degraded within 30 minutes using pronase solution (FIG. 2) and within 5 hours in a collagenase solution (FIG. 3). Both figures show the excellent resistance against enzymatic attack of BD90 and BD45EN. These materials showed hardly no change in weight if they were incubated in one of the enzyme solutions. This indicates that the material was highly crosslinked leading to that all cleavage sites were blocked or that all cleaved fragments were still linked to the DSC matrix.

BDDGE crosslinking at acidic conditions (BD45) is less compared to amine crosslinking, but still shows interesting properties. If amine groups were acetylated after BDDGE crosslinking, very low stabilities were obtained, probably because modification destabilized the triple-helix structure and the material was more prone to enzymatic attack. G-DSC shows rather poor stability, although a normal degree of crosslinking was obtained ($t_{shrinkage}$=69° C.; 12 amine groups are left).

Mechanical Testing. The influence of crosslinking on the final mechanical properties is shown in Table 5. Crosslinking increases the tensile strength and both the low strain and high strain modulus, and decreases the elongation at break and the elongation at alignment. Exceptions are the high elongation at break of GA crosslinked DSC and the tensile strength of BD90, which was not affected during crosslinking.

Figure 5:
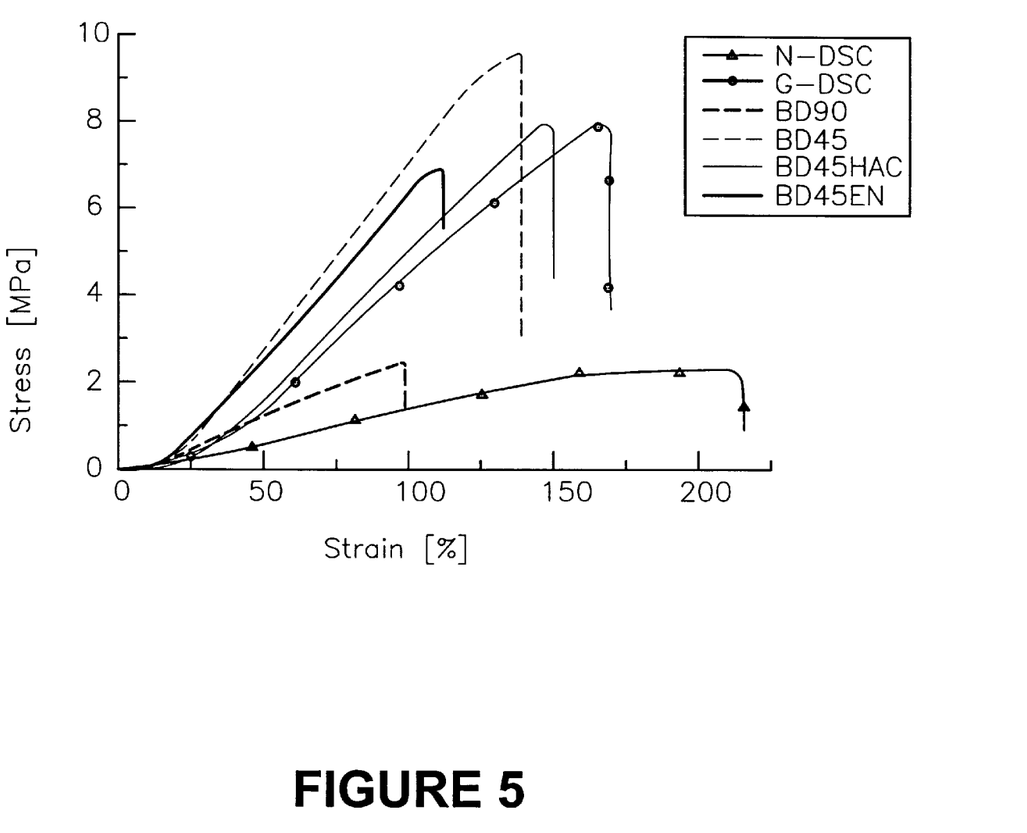
FIG. 5 shows stress-strain curves of noncrosslinked and crosslinked dermal sheep collagens.

The difference between BDDGE crosslinking under acidic conditions (BD45) and under alkaline conditions (BD90) is shown in FIG. 5. Crosslinking via the carboxyl groups showed a much higher tensile strength (9.39 MPa vs. 2.64 MPa) combined with a higher elongation at break (143% vs. 85%) for BD45. Both the low and high strain modulus of the BD45 showed higher values as well.

A second treatment step of BD45 did not alter the mechanical properties that much. If the remaining amine groups were acetylated with HAc-NHS, only the tensile strength and the high modulus strain were decreased. EDC/NHS crosslinking of BD45 retained the good mechanical properties of BD45, except for a reduction (143% to 101%) in the elongation at break.

TABLE 5

Mechanical Characteristics of (Non) Crosslinked DSC.

| Sample | Tensile Strength [Mpa] | Elongation at Break [%] | Elongation at Alignment [%] | Low Strain Modulus [MPa] | High Strain Modulus [MPa} |
|---|---|---|---|---|---|
| N-DSC | 2.61 ± 0.4 | 157 ± 40 | 44 ± 8 | 0.78 ± 0.12 | 2.39 ± 0.4 |
| GDSC | 7.92 ± 0.2 | 209 ± 50 | 34 ± 8 | 2.00 ± 0.4 | 5.66 ± 1.0 |
| BD90 | 2.64 ± 0.1 | 85 ± 10 | 15 ± 2 | 1.79 ± 0.5 | 4.3 ± 0.6 |
| BD45 | 9.39 ± 0.15 | 143 ± 20 | 27 ± 5 | 2.89 ± 0.8 | 9.35 ± 1.0 |
| BD45Hac | 7.14 ± 0.6 | 134 ± 20 | 23 ± 6 | 2.25 ± 0.2 | 6.97 ± 0.6 |
| BD45EN | 7.18 ± 0.5 | 101 ± 5 | 23 ± 1.5 | 2.37 ± 0.4 | 9.51 ± 1.5 |

Discussion

Collagen-based biomaterials are frequently crosslinked with glutaraldehyde (GA) to increase the mechanical properties and to improve the enzymatic resistance. The chemistry of GA crosslinking is not fully understood, but it is clear that the amine groups of the collagen are involved during the crosslink reaction, because after crosslinking a decrease of the free lysine residues is observed in combination with an increase in the shrinkage temperature. It is reported in the literature that GA crosslinked biomaterials were cytotoxic, probably due to the release of monomeric GA molecules. GA also results in a higher stiffness of the biomaterial and induces calcification during implantation, which are unfavorable for bioprosthetic heart valves and vascular grafts.

To overcome the problem involved using GA as a crosslinker, alternative reagents were tested which would crosslink the biomaterial sufficiently, but which show better mechanical properties, less calcification and less cytotoxity.

Polyepoxy compounds have gained attention as crosslinkers during the last years. These reports showed that these reagents are effective crosslinkers, resulting in stabilized biomaterials with good mechanical properties and which showed less calcification during in-vivo studies.

Because epoxide groups are also prone to reaction with carboxyl groups, crosslinking at more acidic solutions resulted in crosslinking via the carboxyl groups. DSC crosslinked at acidic conditions showed complete other macroscopic properties (soft, loose, flexible) than DSC crosslinked at alkaline conditions (stiff, compact). The thermal stability was somewhat lower (62° C. vs. 67° C.), but the mechanical properties were superior (much higher tensile strength and higher elongation at break). However, the enzymatic resistance against bacterial collagenase and pronase were lower. In order to maintain the favorable macroscopic properties of DSC crosslinked at acidic conditions, but to improve its enzymatic resistance, a second additional crosslinking (EDC/NHS) step was performed. The influence of modification of the residual amine groups after the BDDGE crosslinking step was also studied.

Crosslinking of DSC using a water-soluble carbodiimide (1-ethyl-3-(3-demethyl aminopropyl) carbodiimide.HCl (EDC) in combination with N-Hydroxysuccinimide was extensively studied. This crosslinking procedure involves the activation of the carboxyl groups by EDC to give O-acylisourea groups. NHS will convert this O-acylisourea group into an NHS activated carboxylic acid group. Crosslinking is achieved by reaction of this group with an adjacent free amine group. EDC/NHS crosslinked DSC showed very good mechanical properties and enzymatic resistance. Modification of the free amine group using an NHS ester of acetic acid during a second step showed a decrease in thermal stability and a negative change in enzymatic resistance compared to BD45.

Crosslinking using GA resulted in an increase of $T_s$ (45.9° C. to 69.2° C.) in combination with a decrease of the percentage of free amine groups (38.3%). About the same degree of crosslinking was obtained using BDDGE at pH 9.0 ($T_s$=67.0° C. and 46.5% of free amines). BDDGE crosslinking using an acidic pH involves carboxyl groups (BD45) as can be proven by the high percentage of free amines after the crosslinking process (87.4%). A slightly lower $T_s$ was observed (63.5° C.).

Treatment of BD45 with an NHS ester of acetic acid resulted in modification of free amines as can be shown by a decrease of the percentage of free amines from 87.4% to 33.6%. The shrinkage temperature was slightly decreased, which can be explained by destabilization of the triple-helix conformation of the collagen molecules.

EDC/NHS crosslinking increases the $T_s$ from 67° C. to 81° C. This amount of free amines is decreased form 87% to 56.6%, which means that about 30% or 9 amine groups per 1000 aminoacids have reacted. This indicates that additional crosslinks were formed and that two different types of bridges were present in the collagen matrix.

Differential Scanning Calorimetry measurements showed the influence of the crosslinking step on the transition characteristics. Crosslinking in general resulted in a narrower transition peak, showing that the material was more homogeneous after the crosslinking process. This peak was more symmetric indicating that the crosslinks were distributed homogeneously in the collagen matrix. Crosslinking via the carboxyl groups showed a symmetric-like peak, while crosslinking via the amines showed a non-symmetric peak. This can indicate that crosslinking via the amines resulted in a less homogeneous distribution of the crosslinks.

A second treatment (HAc-NHS or EDC/NHS) did not change the transition peak. Acidic crosslinking led to an increase of the transition enthalpy, indicating that crosslinking resulted in a better organization of the collagen molecules. In contrast, amine crosslinking showed a lowering of the enthalpy. BD45EN showed the highest enthalpy (19.3 Joules/gram) meaning that both networks contributed to a better organization of the collagen molecules.

The difference in macroscopic appearance is presented in Table 2. This table shows that especially crosslinking via the amine groups (GA, BD90) results in a stiffer material. The loose and soft matrix which was obtained after crosslinking at an acidic pH was not affected by the second treatment. BD45 showed a rather low hydrolytic stability, which can be explained by the ester bonds which were formed during crosslinking (Scheme 1). EDC/NHS crosslinking improved the resistance against hydrolysis, while acetylation of the amine groups did not affect the stability.

The degradation behavior of collagen-based biomaterials is frequently controlled by chemical crosslinking. The resistance of crosslinked materials against degradation is often studied in vitro using enzymes like collagenase and pronase and is monitored by changes in weight as a function of the digestion time.

Bacterial collagenase from *Clostridium histolicum* is capable of cleaving peptide bonds within the triple helical structure and have a specificity for the Pro-X-Gly-Pro-Y region, splitting between X and Gly. This region is found about 40 times in a α-chain. Pronase (which is a mixture of unspecific endo- and exto proteases) from *Streptomyces grisseus* has the specificity to cleave bonds at the non-helical ends and regions of the matrix. Studies showed that most proteases like pepsin and trypsin were unable to disrupt the native collagen structure but they were capable of releasing non-collagen peptides from tropocollagen. They can cleave the material at the end-chains, the so-called telopeptides. Pronase digestion resulted in some shortening of the helical portion of the tropocollagen (up to a maximum of 25%). The peptides which were released by the pronase differed from collagen in that they contained less glycine and proline and little or no hydroxyproline. These peptides were acidic and rich in tyrosine.

A combination of both degradation tests can give one more information about the stability of the collagen-based material and the location of the crosslinks formed. FIG. 5 shows clearly that crosslinking enhances the stability of the collagen-based material, means that the cleavage sites are blocked or shielded by the crosslinks or that the cleaved fragments are held together by chemical crosslinks. N-DSC was fully degraded within 4 hours, while the crosslinked material still showed some material present in the solution. Remarkable was that GA crosslinked materials showed a faster degradation rate than BDDGE crosslinked materials. BDDGE crosslinking via the amines showed no degradation after 24 hours, while BD45 showed a degradation of about 10%. The destabilization effect of the second modification step (BD45HAc) was observed during this collagenase digestion (20% of the material was still present). Modification of amine groups can result in blocking or shielding of the cleavage sites, but it seems that the collagenase still can penetrate into the fibers and cleave the peptide bonds. From this point, it can be concluded that crosslinking not only results in blocking and shielding of the specific cleavage sites but in formation of a tight network between the fibrils and the helices as well. This tight network prevents the matrix to be solubilized and keeps the fragments together. It might be that the mechanical properties will be decreased even if the remaining weight is 100%. Additional EDC/NHS crosslinking of BD45 results in a material having the same superior enzymatic resistance as BD90.

Crosslinking also improves the resistance against pronase degradation. N-DSC was degraded within 30 minutes. GA crosslinked DSC showed a rather poor resistance against pronase and was degraded within 25 hours. BD90 which had almost the same degree of crosslinking showed almost no degradation within 48 hours. Because pronase cleaves the material more in the non-helical regions of the matrix, it seems that BDDGE crosslinks were formed in the helical but also in the non-helical regions. BD45 showed less resistance against degradation (35% of the initial weight was present), but this resistance was improved after EDC/NHS crosslinking. As expected, HAc-NHS modification led to an increase of the degradation rate. The figures show that collagenase degradation of collagen shows more or less a linear behavior as function of the time. This means a surface degradation process took place. Pronase digestion showed a faster degradation rate during the first stage, indicating that more processes of degradation took place.

Figure 4:
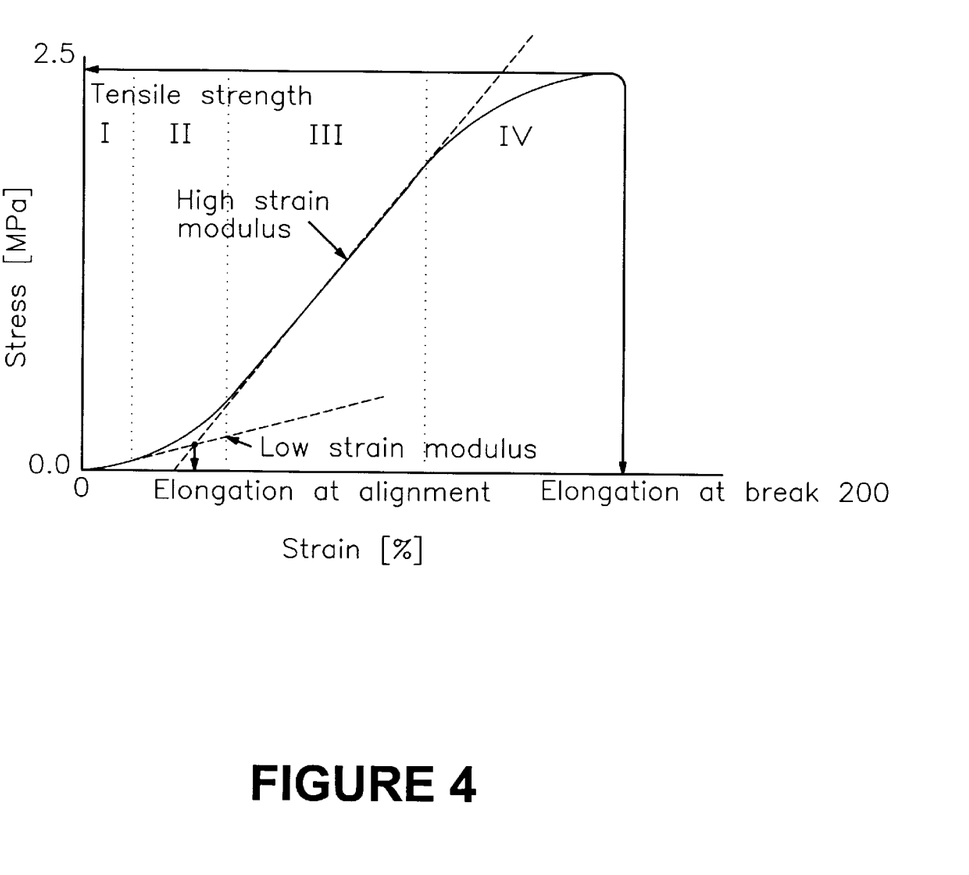
FIG. 4 is a typical stress-strain curve of collagen, depicting four distinctive regions, related to different phenomena taking place in the collagen material when stress is applied.

Crosslinking will also influence the mechanical characteristics of the material. A uniaxial experiment can be performed in order to obtain the stress-strain curve. As shown in FIG. 4, the stress-strain curve can be divided into four distinctive parts. Initially, the fiber bundles are randomly oriented and only small stresses are needed to straighten the bundles (part I, low modulus strain). The initial orientation of the fiber bundles can be expressed as the elongation at alignment. As more and more bundles become taut, an increase in modulus is observed (part II). The linear part of the curve at high strains (III) is called the high modulus strain. At sufficient stress, the material starts to yield and finally breaks (IV).

Crosslinking of DSC improved the mechanical properties of the material, which is shown in Table 4. Several other articles showed that crosslinking of aortic leaflets and bovine pericardium resulted in an increase of the elongation at break after crosslinking. This can be ascribed to the crimping of the fiber bundle network during crosslinking which increased the angle of weave of the fiber bundles, resulting in a higher elongation at alignment and a higher elongation at break.

Besides GA crosslinking which showed an increase of the elongation at break, crosslinking processes decreased the elongation at break. This can be explained by the introduction of the chemical bridges in the matrix. These bridges prevent the fibrils and fibers to orient in the pull direction, resulting in a lower elongation at break. This is also confirmed by comparing the high strain modulus of N-DSC (2.39 MPa) with the values of cross-linked DSC (4.3 MPa–9.51 MPa). This means that a higher force is required to reach a certain elongation.

As shown in FIG. 5, the increase in tensile strength (2.61 MPa to 9.4 MPa) after crosslinking with BDDGE under acidic conditions was observed. It seems that the chemical crosslinking prevent the material to break at relative low stresses, so more fibers could carry the load, resulting in a higher tensile strength. The observed decrease in the elongation at alignment denotes the fact that crosslinking prevents the initial orientation of the fibers when strain is applied. In turn, this means that especially the BDGGE crosslinked DSC comprises molecular bridges formed between the fibers. Introduction of a network between the fibrils and fibers also causes an increased low strain modulus (0.78 MPa to 1.79–2.89 MPa).

The difference between BDDGE crosslinking under acidic (BD45) and alkaline conditions (BD90) is remarkable. Acidic crosslinking showed much better properties (higher elongation at break and tensile strength). Crosslinking via the amines led to a rigid network, which has a more or less brittle character (low elongation at break; 85%). It was demonstrated that application of a second crosslinking step (EDC/NHS) after the epoxide crosslinking at acidic conditions (BD45EN) retained the favorable mechanical properties. The tensile strength and the elongation at break decreased somewhat, most likely caused by introduction of more internal stresses because of the zero-length crosslinking, but mechanical properties remained superior to BD90. Modification of the amines after acidic cross-linking (BD45Ac) showed that only the tensile strength and high strain modulus were negatively affected. In conclusion, both additional steps did not significantly influence the superior mechanical properties of BD45.

The complete disclosure of all patents, patent documents, and publications cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A method for making a bioprosthetic device made of collagen-based material having collagen amine groups and collagen carboxyl groups, the method comprising combining an epoxy functionalized crosslinking agent with the collagen-based material in an aqueous medium at an acidic pH to react a portion of the collagen carboxyl groups with the epoxy functionalized crosslinking agent to form crosslinked collagen-based material comprising residual collagen carboxyl groups.

2. The method of claim 1 further including blocking at least a portion of the collagen amine groups with a blocking agent.

3. The method of claim 2 wherein the step of blocking at least a portion of the collagen amine groups is carried out before the step of combining an epoxy functionalized crosslinking agent with the collagen-based material.

4. The method of claim 2 wherein the blocking agent is selected from the group of an acylating agent, an aminating agent, and a biologically active derivative thereof.

5. The method of claim 4 wherein the step of blocking comprises contacting the collagen amine groups with an acylating agent selected from the group of an N-hydroxy succinimide ester, a p-nitrophenyl ester, 1-acetylimidazole, and citraconic anhydride.

6. The method of claim 2 wherein the step of blocking comprises contacting the collagen amine groups with an aminating agent selected from the group of an aldehyde and a ketone.

7. The method of claim 1 wherein the collagen-based material comprises whole tissue.

8. The method of claim 1 wherein the bioprosthetic implant is a heart valve.

9. The method of claim 1 further comprising a step of activating at least a portion of the residual collagen carboxyl groups to form activated carboxyl groups capable of reacting with collagen amine groups.

10. The method of claim 9 wherein the step of activating comprises reacting at least a portion of the residual collagen carboxyl groups with an activating agent selected from the group of a carbodiimide, an azide, 1,1'-carbonyldiimidazole, N,N'-disuccinimidyl carbonate, 2-ethoxy-1-ethoxycarbonyl-1,2-dihydroquinoline, and 1,2-benzisoxazol-3-yl-diphenyl phosphate, N-ethyl-5-phenylisoxazolium-s'-sulfonate, and mixtures thereof.

11. The method of claim 10 wherein the activating agent is a carbodiimide.

12. The method of claim 11 wherein the carbodiimide is at least partially water soluble.

13. The method of claim 12 wherein the carbodiimide is 1-ethyl-3-(3-dimethylaminopropyl) carbodiimide.HCl.

14. The method of claim 12 wherein the carbodiimide is selected from the group of 1-ethyl-3-(3-dimethylaminopropyl) carbodiimide.HCl, cyanamide, N,N'-dicyclohexylcarbodiimide, N,N'-diisopropylcarbodiimide, 1-cyclohexyl-3-(2-morpholinoethyl) carbodiimide metho-p-toluenesulfonate, and mixtures thereof.

15. The method of claim 9 wherein the step of activating comprises contacting the residual collagen carboxyl groups with an activating agent in the presence of a stabilizing agent.

16. The method of claim 15 wherein the stabilizing agent is selected from the group of N-hydroxysuccinimide, N-hydroxybenzotriazole, N-hydroxy-5-norbornene-endo-2,3-dicarboximide, 4-dimethylaminopyridine, the sulfo-derivative of N-hydroxysuccinimide, and mixtures thereof.

17. The method of claim 9 wherein the step of activating comprises contacting the collagen carboxyl groups with a carbodiimide and N-hydroxysuccinimide.

18. The method of claim 9 wherein the step of activating comprises contacting the residual collagen carboxyl groups with an activating agent in the presence of a spacer.

19. The method of claim 1 wherein the epoxy functionalized crosslinking agent is a polyol polyglycidylether.

20. The method of claim 19 wherein the epoxy functionalized crosslinking agent is selected from the group of glycol diglycidyl ether, glycerol diglycidyl ether, glycerol triglycidyl ether, and butanediglycidyl ether.

21. The method of claim 19 wherein the epoxy functionalized crosslinking agent has the following formula:

wherein R may be any substituent that does not interfere with the crosslinking process and/or diminish the solubility of the crosslinking agent in aqueous solutions and n=1–6.

22. The method of claim 1 wherein the epoxy functionalized crosslinking agent is selected from the group of polyglycidylether-functional molecules of polyethlyeneglycol, polypropyleneglycol, and polyethylenepropyleneglycol, for which the diglycidylether derivative can be represented by the following general formula:

wherein x+z=0–70 and y=0–90.

23. The method of claim 1 wherein the epoxy functionalized crosslinking agent is a polyepoxy crosslinking agent.

24. The method of claim 23 wherein the polyepoxy crosslinking agent is a hydrophilic diepoxide.

25. The method of claim 1 wherein the pH of the aqueous medium is about pH=4.5 to about pH=6.

26. The method of claim 1 further including a step of reacting the residual collagen carboxyl groups with the collagen amine groups to form zero-length crosslinks.

27. The method of claim 1 further including a step of combining a spacer with the crosslinked collagen-based material comprising residual collagen carboxyl groups to form crosslinks between the collagen amine groups.

28. A method for crosslinking collagen-based material having collagen amine groups and collagen carboxyl groups, the method comprising:

combining a diepoxy crosslinking agent with the collagen-based material in an aqueous medium at an acidic pH to react a portion of the collagen carboxyl groups with the diepoxy crosslinking agent to form crosslinked collagen-based material comprising residual collagen carboxyl groups; and contacting at least a portion of the residual collagen carboxyl groups with an activating agent in the presence of a stabilizing agent to form activated carboxyl groups capable of reacting with collagen amine groups.

* * * * *